US012606531B2

(12) United States Patent
Vogt et al.

(10) Patent No.: US 12,606,531 B2
(45) Date of Patent: Apr. 21, 2026

(54) PREPARATION OF SUBSTITUTED 3-ARYL-5-TRIFLUOROMETHYL-1,2,4-OXADIAZOLES

(71) Applicant: BASF SE, Ludwigshafen (DE)

(72) Inventors: Florian Vogt, Ludwigshafen (DE); Kailaskumar Borate, Navi Mumbai (IN); Bernd Wolf, Ludwigshafen (DE); Christopher Koradin, Ludwigshafen (DE); Roland Goetz, Ludwigshafen (DE); Harish Shinde, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 876 days.

(21) Appl. No.: 17/795,941

(22) PCT Filed: Feb. 1, 2021

(86) PCT No.: PCT/EP2021/052257

§ 371 (c)(1),
(2) Date: Jul. 28, 2022

(87) PCT Pub. No.: WO2021/156175

PCT Pub. Date: Aug. 12, 2021

(65) Prior Publication Data

US 2023/0066401 A1 Mar. 2, 2023

(30) Foreign Application Priority Data

Feb. 5, 2020 (EP) .................................... 20155610

(51) Int. Cl.
*C07D 271/06* (2006.01)

(52) U.S. Cl.
CPC .................................. *C07D 271/06* (2013.01)

(58) Field of Classification Search
CPC .................................................... C07D 271/06
See application file for complete search history.

(56) References Cited

FOREIGN PATENT DOCUMENTS

| | | | |
|---|---|---|---|
| WO | WO-2015/185485 | A1 | 12/2015 |
| WO | WO-2017/211649 | A1 | 12/2017 |
| WO | WO-2017/222951 | A1 | 12/2017 |
| WO | WO-2019/020451 | A1 | 1/2019 |
| WO | WO-2019/020501 | A1 | 1/2019 |

OTHER PUBLICATIONS

Durden, et al., "Reaction of "activated" esters with amidoximes. Convenient synthesis of 1,2,4-oxadiazoles", Journal of Organic Chemistry, vol. 36, Issue 9, May 1, 1971. 1306-1307.
European Search Report for EP Patent Application No. 20155610.7, Issued on Jul. 28, 2020, 3 pages.
Hemming, "Product Class 6: 1,2,4-Oxadiazoles", Science of Synthesis, Category 2, Hetarenes and Related Ring Systems, 2004, pp. 127-184.
International Search Report for PCT Patent Application No. PCT/EP2021/052257, Issued on Feb. 22, 2021, 4 pages.

*Primary Examiner* — Shawquia Jackson
(74) *Attorney, Agent, or Firm* — MARSHALL, GERSTEIN & BORUN LLP

(57) ABSTRACT

The present invention relates to a process for the preparation of substituted 3-aryl-5-trifluoromethyl-1,2,4-oxadiazoles of formula (I), which can be obtained through reaction of amidoxime compounds of formula (II) with a haloacetic ester in the presence of a base.

(I)

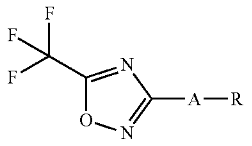

(II)

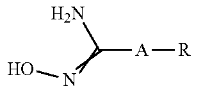

17 Claims, No Drawings

PREPARATION OF SUBSTITUTED 3-ARYL-5-TRIFLUOROMETHYL-1,2,4-OXADIAZOLES

CROSS-REFERENCE TO RELATED APPLICATIONS

This is the U.S. national phase of International Application No. PCT/EP2021/052257, filed Feb. 1, 2021, which claims the benefit of European Patent Application No. 20155610.7, filed on Feb. 5, 2020.

The present invention relates to a process for the preparation of substituted 3-aryl-5-trifluoromethyl-1,2,4-oxadiazoles of formula I, which can be obtained through reaction of amidoxime compounds of formula II with a haloacetic ester in the presence of a base.

I

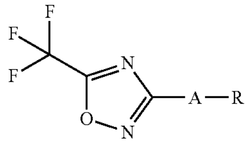

II

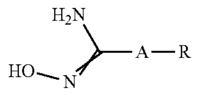

Substituted 3-aryl-5-trifluoromethyl-1,2,4-oxadiazoles are known to be useful for controlling phytopathogenic fungi, for example from WO 2015/185485 A1 and WO 2017/211649 A1.

Typically, the preparation of 3-aryl-5-trifluoromethyl-1,2,4-oxadiazoles involves the formation of the oxadiazole ring through the reaction of amidoxime compounds, for example compounds of formula II, with an activated derivative of trifluoroacetic acid (TFA). In the first reaction step the hydroxy group in compounds of formula II is acylated. Subsequently, the intermediate 0-trifluoroacetyl amidoximes undergo ring closure with concominant elimination of water to form the oxadiazole moiety.

Trifluoroacetic acid anhydride (TFAA) is commonly used as an acylating agent. TFAA is a liquid and not very volatile. It can be handled conveniently on a laboratory scale. In the above reaction at least two equivalents of acylating agent are necessary to ascertain the complete conversion of compounds II. Hence, if TFAA is used, a total amount of at least three equivalents TFA is formed per equivalent of compounds II, which must be discarded. TFAA is rather expensive and for the sake of atom efficiency, there is an interest to reduce the excess amounts of TFA furnished during or after the ring closing reaction.

WO 2019/020451 A1 discloses the use of trifluoroacetic halides instead of TFAA, which results in the formation of a comparatively smaller amount of TFA. The reaction, however, still furnishes significant amounts of TFA along with hydrogen halides, which may cause corrosion of reaction equipment and eventually the hydrogen halides must be separated from the reaction product. Trifluoroacetic halides boil at low temperatures and are thus not easy to handle and, since they are also highly toxic, pose risks for the operator, in particular in large scale setups.

The transformations described in the references above produce considerable amounts of TFA that must be separated from the reaction product and discarded. To increase atom efficiency, trifluoroacetic acid esters may be used in these processes, which are less reactive towards amidoximes of formula II than TFAA or trifluoroacetic halides. In theory, the use of esters instead of the corresponding acid halides or anhydrides requires, if any, only a small excess of the acylating agent.

Durden et al. in Journal of Organic Chemistry 1971, 36, 9, 1306-1307, describe a process, in which (halo)acetic acid vinylesters are used in reactions with benzamidoxime to obtain the corresponding oxadiazoles. The reported yields with trifluoroacetic acid vinylesters are moderate (43%). The authors point out that, when using vinyl trifluoroacetate, a solvent is needed to moderate the initial reaction of the amidoxime with the ester.

In view of the above, it was an object of the present invention to overcome these disadvantages and to provide an improved and more economical and production plant friendly process, which enables the preparation of 3-aryl-5-trifluoromethyl-1,2,4-oxadiazoles on an industrial scale in high yield and with low amounts of side-products.

The inventors surprisingly found that alkylesters of trifluoroacetic acid may be reacted with amidoxime compounds of formula II in the absence of auxiliary solvents, providing excellent yields of the desired oxadiazoles of formula I and in high purity. The reaction furnishes an alkyl alcohol of formula $R^5$—OH, which can be removed from the reaction mixture without greater effort.

The process is eco-friendly and more cost efficient than previously reported processes as it does not require the use of an auxiliary solvent and employs readily available and cheap alkyl esters. Due to the inherent properties of the esters of formula II.a, the process is more convenient, employs non-toxic reagents, is production plant friendly and simplifies the workup procedure.

The reaction product obtained from the reaction between compounds II and II.a is typically a liquid, which is advantageous for a technical setup with continuous reaction processes. The reaction product may be employed in subsequent transformations without the need to change the reaction vessel (one-pot-reaction).

Accordingly, the present invention relates to a process for preparing compounds of formula I,

I

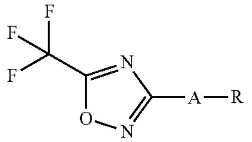

wherein

A is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S; and wherein A is further unsubstituted or further substituted with additional n identical or different radicals $R^A$; wherein n is 0, 1, 2, 3, or 4;

$R^A$ is independently selected from the group consisting of halogen, cyano, $C_1$-$C_6$-alkyl, $C_1$-$C_6$-haloalkyl, $C_1$-$C_6$-alkoxy, and $C_1$-$C_5$-haloalkoxy;

R is methyl, which is further unsubstituted or further substituted with additional 1, 2, or 3 identical or different radicals $R^X$; wherein $R^X$ is hydrogen, halogen, oxo, or OH;

the process comprising reacting an amidoxime compound of formula II,

II

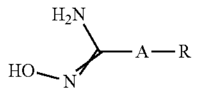

wherein the variables A and R are as defined above for compounds of formula I, with a haloacetic ester of formula II.a, II.a

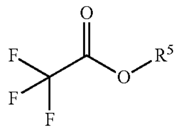

wherein $R^5$ is $C_1$-$C_6$-alkyl; in the presence of a base; characterized in that the process is conducted in the absence of an auxiliary solvent.

The amidoxime compounds of formula II can be obtained from cyano compounds V,

N≡C-A-R V wherein the variables A and R are as defined or preferably defined herein for compounds of formula I or Ib, by treatment with hydroxylamine or its hydrochloride salt, in the presence of a base, preferably triethylamine, sodium hydroxide or sodium methylate, in a suitable solvent, such as methanol, ethanol or water, or a mixture of these solvents, at a temperature between 0° C. and 100° C. For related examples see Kitamura, S. et al *Chem. Pharm. Bull.* 2001, 49, 268 or any one of the patent references cited above. Compounds of formula V are either commercially available or may be prepared using standard procedures known to a person skilled in the art from readily available starting materials.

In one embodiment of the invention radical $R^5$ in haloacetic esters of formula II.a is methyl, ethyl, n-propyl, iso-propyl, or n-butyl; preferably methyl or ethyl; particularly ethyl.

In one embodiment the reaction is conducted using 1 to 6 molar equivalents of the haloacetic ester II.a, based on the amount of the amidoxime 11. Preferably, 1 to 3 molar equivalents are used, particularly 1 to 2 molar equivalents are used, even more preferred 1 to 1.4 molar equivalents are used, based on the amount of the amidoxime 11.

The reaction temperature of the above process is preferably in the range of 0° C. to 100° C.; preferably in the range of from 0° C. to 60° C.; more preferably in the range of from 10° C. to 60° C.; more preferably in the range of from 20° C. to 60° C.; particularly in the range of from 15° C. to 45° C.; particularly in the range of from 20° C. to 45° C.

The reaction is generally carried out within 10 minutes to 16 hours, preferably within 0.5 to 8 hours or within 60 minutes to 12 hours, preferably within 2 to 8 hours, more preferably within 2 to 6 hours.

The process of the present invention is typically carried out at atmospheric pressure.

The process of the present invention is carried out in the presence of a base, which can be an inorganic or an organic base. Examples for preferred inorganic bases are alkali metal and alkaline earth metal carbonates, hydroxides, and phosphates. Preferred alkali metal carbonates are sodium and potassium carbonate, particularly sodium carbonate. Preferred alkaline earth metal carbonates are magnesium and calcium carbonates. Preferred alkali metal hydroxides are sodium and potassium hydroxide, particularly sodium hydroxide. Preferred alkaline earth metal carbonates are magnesium and calcium hydroxide. Preferred alkali metal phosphates are trisodium phosphate ($Na_3PO_4$) and disodium phosphate ($Na_2HPO_4$).

In another aspect the base is an organic base such as tri-($C_1$-$C_6$)-alkylamines or an N-heteroaromat. Examples for tri-($C_1$-$C_6$)-alkylamines are, for example, trimethylamine, triethylamine, tripropylamine, tributylamine, trihexylamine, trioctylamine, tridecylamine, N,N-dimethylethylamine, dimethylpropylamine; aromatic amines such as dimethylaniline or tribenzylamine; cyclic amines such as N-methylpyrrolidine, N-methylpiperidine, N-methylmorpholine, N,N'-dimethylpiperazine.

Also suitable are N-heteroaromatic bases such as pyridine, imidazole, N-methylimidazole or quinoline. Examples of suitable substituted pyridines are collidine, lutidines, 2-picoline, 3-picoline, 4-picoline, N,N-dimethyl-4-aminopyridine, 5-ethyl-2-methyl-pyridine.

Further suitable bases are 1,5,7-triazabicyclo[4.4.0]dec-5-ene (TBD), and 1,8-diazabicyclo[5.4.0]undec-7-ene (DBU).

In one embodiment the process of the present invention is carried out in the presence of a base, which is selected from the group consisting of alkali metal $C_1$-$C_6$-alkoxides, alkali and earth alkali metal carbonates, alkali and earth alkali metal hydroxides, tri-($C_1$-$C_6$)-alkylamines, pyridine, N-methylimidazole or quinoline, pyridine, collidine, lutidine, 2-picoline, 3-picoline, 4-picoline, N,N-dimethyl-4-aminopyridine, 5-ethyl-2-methyl-pyridine, DBU and TBD.

In one aspect the base is selected from the group consisting of alkali metal $C_1$-$C_6$-alkoxides; particularly sodium methoxide or sodium ethoxide.

The base is used in an amount of at least 80 mol % based on the amount of the compound of formula II, or at least 100 mol %, or at least 150 mol %. In another aspect of the present invention the base is used in an amount that ranges between 80 and 1000 mol % based on the amount of the compound of formula II. In a further aspect of the present invention the base is used in an amount that ranges between 80 and 500 mol % based on the amount of the compound of formula II. In yet another aspect the base is used in an amount that ranges between 90 and 200 mol % based on the amount of the compound of formula II.

In one aspect of the present invention the variable A is phenyl.

In one embodiment of the present invention radical $R^A$ is halogen, $C_1$-$C_6$-alkyl, $C_1$-$C_6$-haloalkyl, $C_1$-$C_6$-alkoxy, or $C_1$-$C_6$-haloalkoxy; particularly fluorine.

In a preferred embodiment the variable n is 0.

In one preferred aspect of the present invention the variable R is methyl, chloromethyl, dichloromethyl, or trichloromethyl; particularly methyl.

In one aspect $R^A$ is fluorine; n is 1; R is methyl, chloromethyl, dichloromethyl, or trichloromethyl.

In one aspect the present invention relates to a process as defined above, wherein the amidoxime is of formula II.b, II.b

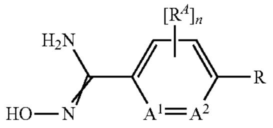

wherein n corresponds to the total number of radicals $R^A$ attached to the central aromatic ring and wherein n is 0 or 1; $A^1$ and $A^2$ are independently selected from nitrogen, C—H, or C—$R^A$; and wherein no more than one of $A^1$ and $A^2$ is nitrogen; and wherein the meaning of R is as defined or preferably defined herein for compounds of formula I; and wherein $R^A$ is selected from the group consisting of halogen, $C_1$-$C_6$-alkyl, $C_1$-$C_6$-haloalkyl, $C_1$-$C_6$-alkoxy, and $C_1$-$C_6$-haloalkoxy; to obtain oxadiazole compounds of formula I.b, I.b

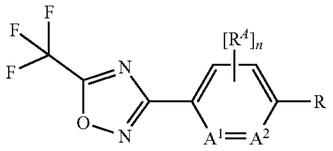

wherein the variables n, $R^A$, $A^1$, $A^2$, and R have the meaning as defined for compounds II.b.

In one embodiment the variables $A^1$ and $A^2$ in compounds of formula I.b and II.b are C—H.

In another embodiment $R^A$ is fluorine and the variables $A^1$ and $A^2$ in compounds of formula I.b and II.b are C—H.

In a preferred embodiment n is 0 and $A^1$ and $A^2$ in compounds of formula I.b and II.b are C—H.

In a preferred embodiment n is 0; $A^1$ and $A^2$ in compounds of formula I.b and II.b are C—H; and R is methyl.

In a further embodiment a compound of formula I or I.b, wherein R is methyl, is converted into valuable chemical products or intermediates.

Accordingly, in one embodiment, compounds of formula I.b, wherein, n is 0, $A^1$ and $A^2$ are C—H, R is methyl, can be further chlorinated to obtain a compound of formula I.c I.c

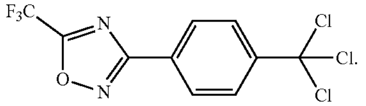

The chlorination of the methyl group R of compounds of formula I or I.b can be achieved as described in WO 2019/020451 A1 and the references cited therein.

In a further embodiment the compound of formula I.c is hydrolyzed to obtain a compound of formula III

III

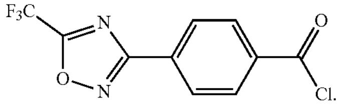

In one embodiment this transformation is carried out in the presence of catalytic amounts of a Lewis acid and water to obtain a compound of formula III, as described in WO 2019/020451 A1 and the references cited therein. Preferably, the Lewis acid is a metal salt, for example aluminum(II) chloride or iron(III) chloride, particularly iron(III) chloride.

In one embodiment, the compound of formula III is reacted with an amine of formula IV, $R^1$—NH—$R^2$ IV wherein $R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—$C_1$-$C_6$-alkoxy, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_3$-cycloalkyl, —$NHSO_2$—$C_1$-$C_4$-alkyl, (C═O)—$C_1$-$C_6$-alkyl, C(═O)—$C_1$-$C_6$-alkoxy, $C_1$-$C_6$-alkylsulfonyl, hydroxy$C_1$-$C_4$-alkyl, C(═O)—$NH_2$, C(═O)—NH($C_1$-$C_4$-alkyl), $C_1$-$C_4$-alkylthio-$C_1$-$C_4$-alkyl, amino$C_1$-$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O)H, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

to obtain a compound of formula V

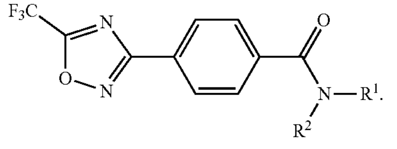

V

These transformations are also described in WO 2019/020451 A1 and the references cited therein.

In another embodiment, the compound of formula V is used to obtain a compound of formula VI

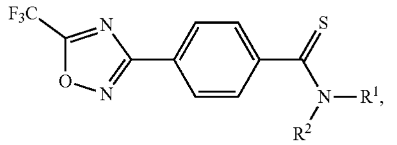

VI as described in WO 2019/020451 A1 and the references cited therein.

In a preferred embodiment the variables $R^1$ and $R^2$ in compounds of formula IV, V and VI have the following meaning:

$R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, OH, $NH_2$, methyl, ethyl, methoxy, trifluoromethyl, trifluoromethoxy, difluoromethyl, difluoromethoxy, and cyclopropyl; and $R^2$ is hydrogen, methyl, or ethyl.

In another preferred embodiment the variables $R^1$ and $R^2$ in compounds of formula IV, V and VI have the following meaning:

$R^1$ is methyl, 2-methoxyiminoethyl, bicyclo[1.1.1]pentan-1-yl, 2-fluoro-phenyl, 4-fluoro-phenyl, or 2,4-difluorophenyl; in particular methyl or 2-fluoro-phenyl; and $R^2$ is hydrogen.

In a preferred embodiment (embodiment E.1) of the present invention the process employs haloacetic esters of formula II.a, wherein radical $R^5$ is methyl or ethyl.

Embodiment E.2: is based on embodiment E.1, wherein 1 to 6 molar equivalents of the haloacetic ester II.a are used, based on the amount of the amidoxime II.

Embodiment E.3: is based on embodiment E.2, wherein the base is selected from the group consisting of alkali metal $C_1$-$C_6$-alkoxides, alkali and earth alkali metal carbonates, alkali and earth alkali metal hydroxides, tri-($C_1$-$C_6$)-alkylamines, pyridine, N-methylimidazole or quinoline, pyridine, collidine, lutidine, 2-picoline, 3-picoline, 4-picoline, N,N-dimethyl-4-aminopyridine, 5-ethyl-2-methyl-pyridine, DBU, and TBD.

Embodiment E.4: is based on embodiment E.3, wherein the base is used in an amount that ranges between 90 and 200 mol %, based on the amount of the compound of formula II.

Embodiment E.5: is based on embodiment E.4, wherein the process is conducted at a temperature between 20° C. and 45° C.

Embodiment E.6: is based on embodiment E.5, wherein in compounds of formula IV, V and VI $R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, OH, $NH_2$, methyl, ethyl, methoxy, trifluoromethyl, trifluoromethoxy, difluoromethyl, difluoromethoxy, and cyclopropyl; and $R^2$ is hydrogen, methyl, or ethyl.

Embodiment E.7: is based on embodiment E.5, wherein in compounds of formula IV, V and VI $R^1$ is methyl, 2-methoxyiminoethyl, bicyclo[1.1.1]pentan-1-yl, 2-fluoro-phenyl, 4-fluoro-phenyl, or 2,4-difluorophenyl; in particular methyl or 2-fluoro-phenyl; and $R^2$ is hydrogen.

The term "auxiliary solvent" herein refers to a compound, which acts as a solvent and is not taking part in the reaction, i.e. a compound that is not identical with the reactants such as the amidoxime II and the haloacetic ester of formula I.a.

In the definitions of the variables given above, collective terms are used which are generally representative for the substituents in question.

The term "$C_n$-$C_m$" indicates the number of carbon atoms possible in each case in the substituent or substituent moiety in question.

The term "halogen" refers to fluorine, chlorine, bromine and iodine.

The term "oxo" refers to an oxygen atom =O, which is bound to a carbon atom or sulfur atom, thus forming, for example, a ketonyl —C(=O)— or sulfinyl —S(=O)— group.

The term "$C_1$-$C_6$-alkyl" refers to a straight-chained or branched saturated hydrocarbon group having 1 to 6 carbon atoms, for example methyl, ethyl, propyl, 1-methylethyl, butyl, 1-methylpropyl, 2-methylpropyl, and 1,1-dimethylethyl.

The term "$C_2$-$C_6$-alkenyl" refers to a straight-chain or branched unsaturated hydrocarbon radical having 2 to 6 carbon atoms and a double bond in any position, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond, such as ethynyl, 1-propynyl, 2-propynyl (propargyl), 1-butynyl, 2-butynyl, 3-butynyl, 1-methyl-2-propynyl.

The term "$C_1$-$C_6$-haloalkyl" refers to a straight-chained or branched alkyl group having 1 to 6 carbon atoms (as defined above), wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2—C_2F_5$, $CF_2—C_2F_5$, $CF(CF_3)_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl.

The term "$C_1$-$C_6$-alkoxy" refers to a straight-chain or branched alkyl group having 1 to 6 carbon atoms (as defined above) which is bonded via an oxygen, at any position in the alkyl group, for example methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy group as defined above, wherein some or all of the hydrogen atoms may be replaced by halogen atoms as mentioned above, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2—C_2F_5$, $OCF_2—C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

The terms "phenyl-$C_1$-$C_4$-alkyl or heteroaryl-$C_1$-$C_4$-alkyl" refer to alkyl having 1 to 4 carbon atoms (as defined above), wherein one hydrogen atom of the alkyl radical is replaced by a phenyl or hetereoaryl radical respectively.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_4$-alkylthio-$C_1$-$C_4$-alkyl" refers to alkyl having 1 to 4 carbon atoms (as defined above), wherein one hydrogen atom of the alkyl radical is replaced by a $C_1$-$C_4$-alkylthio group.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-haloalkylthio" as used herein refers to straight-chain or branched haloalkyl group having 1 to 6 carbon atoms (as defined above) bonded through a sulfur atom, at any position in the haloalkyl group.

The term "$C_1$-$C_4$-alkoxyimino" refers to a divalent imino radical ($C_1$-$C_4$-alkyl-O—N═) carrying one $C_1$-$C_4$-alkoxy group as substituent, e.g. methylimino, ethylimino, propylimino, 1-methylethyl-imino, butylimino, 1-methylpropylimino, 2-methylpropylimino, 1,1-dimethylethylimino and the like.

The term "$C_1$-$C_6$-alkoxyimino-$C_1$-$C_4$-alkyl" refers to alkyl having 1 to 4 carbon atoms, wherein two hydrogen atoms of one carbon atom of the alkyl radical are replaced by a divalent $C_1$-$C_6$-alkoxyimino radical ($C_1$-$C_6$-alkyl-O—N═) as defined above.

The term "$C_2$-$C_6$-alkenyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkenyloxyimino radical ($C_2$-$C_6$-alkenyl-O—N═).

The term "$C_2$-$C_6$-alkynyloxyimino-$C_1$-$C_4$-alkyl" refers to alkyl having 1 to 4 carbon atoms, wherein two hydrogen atoms of one carbon atom of the alkyl radical are replaced by a divalent $C_2$-$C_6$-alkynyloxyimino radical ($C_2$-$C_6$-alkynyl-O—N═).

The term "hydroxy$C_1$-$C_4$-alkyl" refers to alkyl having 1 to 4 carbon atoms, wherein one hydrogen atom of the alkyl radical is replaced by a OH group.

The term "amino$C_1$-$C_4$-alkyl" refers to alkyl having 1 to 4 carbon atoms, wherein one hydrogen atom of the alkyl radical is replaced by a $NH_2$ group.

The term "$C_1$-$C_6$-alkylamino" refers to an amino group, which is substituted with one residue independently selected from the group that is defined by the term $C_1$-$C_6$-alkyl. Likewise, the term "di$C_1$-$C_6$-alkylamino" refers to an amino group, which is substituted with two residues independently selected from the group that is defined by the term $C_1$-$C_5$-alkyl.

The term "$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $C_1$-$C_4$-alkyl-NH-group which is bound through the nitrogen. Likewise, the term "di$C_1$-$C_4$-alkylamino-$C_1$-$C_4$-alkyl" refers to refers to alkyl having 1 to 4 carbon atoms (as defined above), wherein one hydrogen atom of the alkyl radical is replaced by a $(C_1$-$C_4$-alkyl$)_2N$— group which is bound through the nitrogen.

The term "aminocarbonyl-$C_1$-$C_4$-alkyl" refers to alkyl having 1 to 4 carbon atoms, wherein one hydrogen atom of the alkyl radical is replaced by a —(C═O)—$NH_2$ group.

The term "$C_3$-$C_{11}$-cycloalkyl" refers to a monocyclic, bicyclic or tricyclic saturated univalent hydrocarbon radical having 3 to 11 carbon ring members that is connected through one of the ring carbon atoms by substitution of one hydrogen atom, such as cyclopropyl ($C_3H_5$), cyclobutyl, cyclopentyl, cyclohexyl, cycloheptyl, cyclooctyl, bicyclo[1.1.0]butyl, bicyclo[2.1.0]pentyl, bicyclo[1.1.1]pentyl, bicyclo[3.1.0]hexyl, bicyclo[2.1.1]hexyl, norcaranyl (bicyclo[4.1.0]heptyl) and norbornyl (bicyclo[2.2.1]heptyl).

The terms "—C(═O)—$C_1$-$C_6$-alkyl", "—C(═O)—O—$C_1$-$C_6$-alkyl" and "—C(═O)—$C_3$-$C_{11}$-cycloalkyl" refer to aliphatic radicals which are attached through the carbon atom of the —C(═O)— group.

The term "aliphatic" refers to compounds or radicals composed of carbon and hydrogen and which are non-aromatic compounds. An "alicyclic" compound or radical is an organic compound that is both aliphatic and cyclic. They contain one or more all-carbon rings which may be either saturated or unsaturated, but do not have aromatic character.

The terms "cyclic moiety" or "cyclic group" refer to a radical which is an alicyclic ring or an aromatic ring, such as, for example, phenyl or heteroaryl.

The term "and wherein any of the aliphatic or cyclic groups are unsubstituted or substituted with . . . " refers to aliphatic groups, cyclic groups and groups, which contain an aliphatic and a cyclic moiety in one group, such as in, for example, $C_3$-$C_3$-cycloalkyl-$C_1$-$C_4$-alkyl; therefore a group which contains an aliphatic and a cyclic moiety both of these moieties may be substituted or unsubstituted independently of each other.

The term "phenyl" refers to an aromatic ring systems including six carbon atoms (commonly referred to as benzene ring.

The term "heteroaryl" refers to aromatic monocyclic or polycyclic ring systems including besides carbon atoms, 1, 2, 3 or 4 heteroatoms independently selected from the group consisting of N, O and S.

The term "saturated 3- to 7-membered carbocycle" is to be understood as meaning monocyclic saturated carbocycles having 3, 4 or 5 carbon ring members. Examples include cyclopropyl, cyclopentyl, cyclohexyl, cycloheptyl, and the like.

The term "3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms", is to be understood as meaning both, aromatic mono- and bicyclic heteroaromatic ring systems, and also saturated and partially unsaturated heterocycles, for example:

a 3- or 4-membered saturated heterocycle which contains 1 or 2 heteroatoms from the group consisting of N, O and S as ring members such as oxirane, aziridine, thiirane, oxetane, azetidine, thiethane, [1,2]dioxetane, [1,2]dithietane, [1,2] diazetidine;

and a 5- or 6-membered saturated or partially unsaturated heterocycle which contains 1, 2 or 3 heteroatoms from the group consisting of N, O and S as ring members such as 2-tetrahydro-furanyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" or the term "5- or 6-membered aromatic heterocycle" refer to aromatic ring systems including besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

WORKING EXAMPLES

The present invention is further illustrated by means of the following working examples.

Analytical method: HPLC Agilent 1100 Series; column: Agilent Zorbax Phenyl-Hexyl 1.8 μm 50*4.6 mm, Column Flow: 1 mL/min, time: 25 min, pressure: 20000 kPa; temperature: 20° C.; wavelength 200 nm; injector volume: 2 uL; retention time of the respective products is based on reference material and given in the table below.

Eluent: A: Water with 0.1 vol % $H_3PO_4$; B: Acetonitrile

| Time (min) | % B | Rate (mL/min) |
|---|---|---|
| 0.0 | 14 | 1.0 |
| 16.0 | 86 | 1.0 |
| 20.0 | 86 | 1.0 |
| 20.1 | 14 | 1.0 |

Example 1) Preparation of 3-(p-tolyl)-5-(trifluoromethyl)-1,2,4-oxadiazole

A reaction vessel was charged with 40 g (259 mmol) solid N'-hydroxy-4-methyl-benzamidine and 184 g (1.30 mol) of ethyl trifluoroacetate at 22° C. 16.8 g solid sodium methylate (311 mmol) was added in 3 portions over a period of 40 minutes while maintaining a temperature below 33° C. The resulting mixture was stirred for an additional 90 min before 8.8 g hydrogen chloride (1 M in water) was added to adjust the pH to 4. The volatiles were removed under reduced pressure and the distillation sump was washed with water (80 g). After phase separation the tile compound was isolated in a yield of 94.8% and a purity of 92.7% (w/w).

Retention time: 11.2 min.

Example 2) Preparation of 3-[4-(trichloromethyl) phenyl]-5-(trifluoromethyl)-1,2,4-oxadiazole 300 g (1.31 mol) 3-(p-tolyl)-5-(trifluoromethyl)-1,2,4-oxadiazole was placed in a 500 mL quartz glass round bottom flask. 427 g chlorine (6.0 mol) was passed into the reactor, heated to 125° C., and irradiated with a Heraeus TQ 150 Watt (mercury medium pressure emitter) UV-lamp over 8 hours. After completion of the reaction the reaction mass was stripped with nitrogen to remove remaining chlorine and hydrogen chloride gas. GC analysis showed 98.7 ar % product. Yield: 437 g crystalline product; 99%; melting point: 75-78° C.; $^1$H-NMR ($CDCl_3$): 8.1 ppm (m, 2H, 2×CH); 8.3 ppm (m, 2H, 2×CH).

Example 3) Preparation of N-(2-fluorophenyl)-4-[5-(trifluoromethyl)-1,2,4-oxadiazol-3-yl]benzamide 150 g (0.446 mol) solid 3-[4-(trichloromethyl)phenyl]-5-(trifluoromethyl)-1,2,4-oxadiazole and 3.75 g (0.023 mol) iron(III)-chloride was filled in a 0.75 L reactor equipped with an overhead stirrer, reflux condenser and off-gas scrubber. The reactor was heated to 120° C. and 7.6 g (0.422 mol) water was dosed into the reaction mixture within 3 hours and stirred for another 30 minutes. Then the reaction mixture was cooled to 25° C. and 300 g (4.156 mol) tetrahydrofuran was added and the reaction mixture cooled to 10° C. Then a solution of 56 g 2-fluoro-aniline (0.489 mol), 50 g triethylamine (0.489 mol) and 200 g tetrahydrofuran (2.771 mol) was added in about 40 minutes, whereas the temperature of the reaction mixture was kept between 10° C. and 25° C. and the lines were flushed with 100 g (1.4 mol) tetrahydrofuran. After stirring overnight, the mixture was cooled to 5° C. and 450 mL water was added. The solid was filtered off and washed twice with 100 g cold water. A solid material was obtained, which was dried (80° C., 2 kPa) to yield 130 g (0.363 mol) of the title product. HPLC analysis showed >98 ar % product.

Example 4) Preparation of N-methyl-4-[5-(trifluoromethyl)-1,2,4-oxadiazol-3-yl]benzamide 5 g (0.015 mol) solid 3-[4-(trichloromethyl)phenyl]-5-(trifluoromethyl)-1,2,4-oxadiazole and 0.12 g (0.74 mmol) iron(III)-chloride was filled in a 0.75 L reactor equipped with an overhead stirrer, reflux condenser and off-gas scrubber. The reactor was heated to 85° C. and 0.26 g (0.014 mol) water were dosed into the reaction mixture within 1 hour and stirred for another 40 minutes. Then the temperature was cooled to 25° C. and 14.6 g (0.222 mol) tetrahydrofuran was added and the reaction mixture cooled to 0° C. Then 27 mL (5M, 0.074 mmol) of a methylamine solution in tetrahydrofuran was added and stirred overnight at room temperature. Water and ethyl acetate were added and the phases separated. The organic phase was washed with water and dried over magnesium sulfate/activated carbon. Filtration and removal of the volatiles yielded 2.9 g (88 ar %, 0.091 mol, retention time=0.93 min, M+=271) N-methyl-4-[5-(trifluoromethyl)-1,2,4-oxadiazol-3-yl]benzamide.

Example 5) Preparation of N-methyl-4-[5-(trifluoromethyl)-1,2,4-oxadiazol-3-yl]benzenecarbothioamide 15 g (54.8 mmol) N-methyl-4-[5-(trifluoromethyl)-1,2,4-oxadiazol-3-yl]benzamide and 3.8 g (16.9 mmmol) phosphorus(V) sulfide was dissolved in 87 g toluene and heated to 112° C. for 1 hour. The reaction mixture was treated below 100° C. with 100 g water and 100 g toluene. After phase separation at 75° C. the organic phase was separated and washed with 100 g water. The volatiles were removed in vacuo (80° C., 200 to 5 mbar) to yield 15.8 g of crude product, which was suspended in 50 mL diisopropylether and heated to 60° C. for 1 hour. After cooling to room temperature, the precipitate was filtered off and washed with 20 mL diisopropylether. After drying at 80° C. and at reduced pressure, 13.5 g (44.2 mmol, 94 ar %) N-methyl-4-[5-(trifluoromethyl)-1,2,4-oxadiazol-3-yl]benzenecarbothioamide was obtained. $^1$H-NMR (δ/ppm, $CDCl_3$, 400 MHz): 3.4 ppm, s, 3H; 7.8, s, br 1H; 7.9, d, 2H; 8.1, d, 2H).

The invention claimed is:

1. A process for preparing an oxadiazole compound of formula I,

I

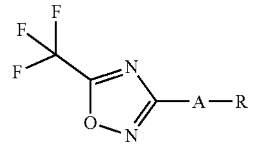

wherein

A is phenyl or a 5- or 6-membered aromatic heterocycle; wherein the ring member atoms of the aromatic heterocycle include besides carbon atoms 1, 2, 3, or 4 heteroatoms selected from N, O, and S as ring member atoms with the provision that the heterocycle cannot contain 2 contiguous atoms selected from O and S;

and wherein A is further unsubstituted or further substituted with additional n identical or different radicals $R^A$; wherein n is 0,1, 2, 3, or 4;

$R^A$ is independently selected from the group consisting of halogen, cyano, $C_1$-$C_6$-alkyl, $C_1$-$C_6$-haloalkyl, $C_1$-$C_6$-alkoxy, and $C_1$-$C_6$-haloalkoxy;

R is methyl, which is further unsubstituted or further substituted with additional 1, 2, or 3 identical or different radicals $R^X$; wherein $R^X$ is hydrogen, halogen, oxo, or OH;

the process comprising reacting an amidoxime compound of formula II,

II

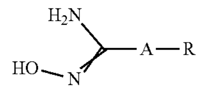

wherein the variables A and R are as defined above for compounds of formula I, with a haloacetic ester of formula II.a, II.a

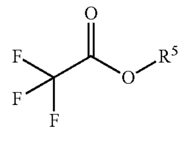

wherein $R^5$ is $C_1$-$C_6$-alkyl; in the presence of a base; wherein the process is conducted in the absence of an auxiliary solvent.

2. The process according to claim 1, wherein $R^5$ in the haloacetic ester II.a is methyl or ethyl.

3. The process according to claim 1, wherein 1 to 6 molar equivalents of the haloacetic ester II.a are used, based on the amount of the amidoxime II.

4. The process according to claim 1, wherein the base is selected from the group consisting of alkali metal $C_1$-$C_6$-alkoxides, alkali and earth alkali metal carbonates, alkali and earth alkali metal hydroxides, tri-($C_1$-$C_6$)-alkylamines, pyridine, N-methylimidazole or quinoline, pyridine, collidine, lutidine, 2-picoline, 3-picoline, 4-picoline, N,N-dimethyl-4-aminopyridine, 5-ethyl-2-methyl-pyridine, DBU, and TBD.

5. The process according to claim 1, wherein the base is used in an amount that ranges between 90 and 200 mol %, based on the amount of the compound of formula II.

6. The process according to claim 1, wherein the process is conducted at a temperature between 20° C. and 45° C.

7. The process according to claim 1, wherein the amidoxime compound is of formula II.b, II.b

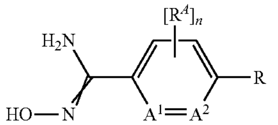

wherein n corresponds to the total number of radicals $R^A$ attached to the central aromatic ring and wherein n is 0 or 1; $A^1$ and $A^2$ are independently selected from nitrogen, C—H, or C—$R^A$; and wherein no more than one of $A^1$ and $A^2$ is nitrogen; and wherein the meaning of R is as defined herein for compounds of formula I; and wherein $R^A$ is selected from the group consisting of halogen, $C_1$-$C_6$-alkyl, $C_1$-$C_6$-haloalkyl, $C_1$-$C_6$-alkoxy, and $C_1$-$C_6$-haloalkoxy; to obtain oxadiazole compounds of formula I.b, I.b

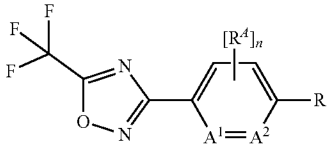

wherein the variables n, $R^A$, $A^1$, $A^2$, and R have the meaning as defined for compounds II.b.

8. The process according to claim 7, wherein $A^1$ and $A^2$ are C—H and $R^A$ is fluorine.

9. The process according to claim 7, wherein n is 0; $A^1$ and $A^2$ are C—H.

10. The process according to claim 1, wherein $R^A$ is fluorine; n is 0 or 1; R is methyl, chloromethyl, dichloromethyl, or trichloromethyl.

11. The process according to claim 7, wherein n is 0; A1 and A2 are C—H; and R is methyl in compounds of formula I.b and II.b; further comprising reacting the compound of formula I.b to obtain a compound of formula I.c I.c

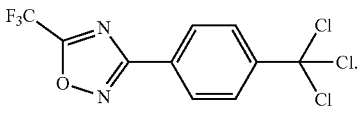

12. The process according to claim 9, further comprising reacting the compound of formula I.c to obtain a compound of formula III

III

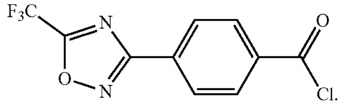

13. The process according to claim 12, wherein the step of reacting the compound of formula I.c to obtain a compound of formula III is carried out in the presence of iron (III) chloride and water.

14. The process according to claim 12, further comprising the step of reacting the compound of formula III with a compound of formula IV, $R^1$—NH—$R^2$ IV wherein $R^1$ is $C_1$-$C_6$-alkyl, $C_1$-$C_6$-alkoxy, $C_3$-$C_{11}$-cycloalkyl, $C_3$-$C_8$-cycloalkenyl, $C_2$-$C_6$-alkenyl, $C_2$-$C_6$-alkynyl, $C_1$-$C_6$-alkoxyimino-$C_1$-$C_4$-alkyl, $C_2$-$C_6$-alkenyloxyimino-$C_1$-$C_4$-alkyl, $C_2$-$C_6$-alkynyloxyimino-$C_1$-$C_4$-alkyl, $C_1$-$C_6$-alkylamino, di$C_1$-$C_6$-alkylamino, —C(═O)—$C_1$-$C_6$-alkyl, —C(═O)—O—$C_1$-$C_6$-alkyl, phenyl-$C_1$-$C_4$-alkyl, phenyl-$C_1$-$C_4$-alkenyl, phenyl-$C_1$-$C_4$-alkynyl, heteroaryl-$C_1$-$C_4$-alkyl, phenyl, naphthyl, or a 3- to 10-membered saturated, partially unsaturated or aromatic mono- or bicyclic heterocycle, wherein the ring member atoms of said mono- or bicyclic heterocycle include besides carbon atoms further 1, 2, 3 or 4 heteroatoms selected from N, O and S as ring member atoms with the provision that the heterocycle cannot contain 2 contiguous atoms selected from O and S; and wherein the heteroaryl group in the group heteroaryl-$C_1$-$C_4$-alkyl is a 5- or 6-membered aromatic heterocycle, wherein the ring member atoms of the heterocyclic ring include besides carbon atoms 1, 2, 3 or 4 heteroatoms selected from N, O, and S as ring member atoms with the provision that the heterocycle cannot contain 2 contiguous atoms selected from O and S; and wherein any of the above-mentioned aliphatic or cyclic groups are unsubstituted or substituted with 1, 2, 3, or up to the maximum possible number of identical or different groups $R^{1a}$; or $R^1$ and $R^2$, together with the nitrogen atom to which they are attached, form a saturated or partially unsaturated mono- or bicyclic 3- to 10-membered heterocycle, wherein the heterocycle includes beside one nitrogen atom and one or more carbon atoms no further heteroatoms or 1, 2 or 3 further heteroatoms independently selected from N, O, and S as ring member atoms with the provision that the heterocycle cannot contain 2 contiguous atoms selected from O and S; and wherein the heterocycle is unsubstituted or substituted with 1, 2, 3, 4, or up to the maximum possible number of identical or different groups $R^{1a}$; wherein $R^{1a}$ is halogen, oxo, cyano, $NO_2$, OH, SH, $NH_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, —$NHSO_2$-$C_1$-$C_4$-alkyl, (C═O)—$C_1$-$C_4$-alkyl, C(═O)—O—$C_1$-$C_4$-alkyl, $C_1$-$C_6$-alkylsulfonyl, hydroxy$C_1$-$C_4$-alkyl, C(═O)—$NH_2$, C(═O)—NH($C_1$-$C_4$-alkyl), $C_1$-$C_4$-alkylthio-$C_1$-$C_4$-alkyl, amino$C_1$-

$C_4$-alkyl, $C_1$-$C_4$-alkylamino-$C_1$-$C_4$-alkyl, di$C_1$-$C_4$-alkylamino-$C_1$-$C_4$-alkyl, aminocarbonyl-$C_1$-$C_4$-alkyl, or $C_1$-$C_4$-alkoxy-$C_1$-$C_4$-alkyl;

$R^2$ is hydrogen, $C_1$-$C_6$-alkyl, $C_2$-$C_6$-alkenyl, $C_2$-$C_6$-alkynyl, $C_1$-$C_6$-alkoxy, $C_3$-$C_{11}$-cycloalkyl, —C(═O) H, —C(═O)—$C_1$-$C_6$-alkyl, —C(═O)—$C_3$-$C_{11}$-cycloalkyl, or —C(═O)—O—$C_1$-$C_6$-alkyl; and wherein any of the aliphatic or cyclic groups in $R^2$ are unsubstituted or substituted with 1, 2, 3, or up to the maximum possible number of identical or different radicals selected from the group consisting of halogen, hydroxy, oxo, cyano, $C_1$-$C_6$-alkyl, $C_1$-$C_6$-alkoxy, and $C_3$-$C_{11}$-cycloalkyl;

to obtain a compound of formula V

V

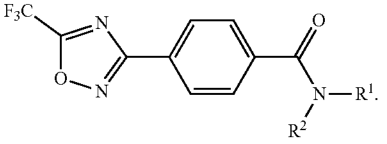

15. The process according to claim 14, further comprising reacting the compound of formula V to obtain a compound of formula VI

VI

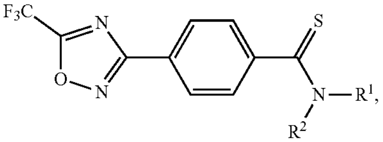

16. The process according to claim 14, wherein in compounds of formula IV, V and VI $R^1$ is methyl, ethyl, n-propyl, iso-propyl, n-butyl, sec-butyl, iso-butyl, cyclopropyl, 2-methoxyiminoethyl, bicyclo[1.1.1]pentan-1-yl, or phenyl; and wherein the phenyl group is unsubstituted or substituted with 1, 2, 3 or up to the maximum possible number of identical or different radicals selected from the group consisting of fluorine, chlorine, cyano, OH, $NH_2$, methyl, ethyl, methoxy, trifluoromethyl, trifluoromethoxy, difluoromethyl, difluoromethoxy, and cyclopropyl; and $R^2$ is hydrogen, methyl, or ethyl.

17. The process according to claim 14, wherein in compounds of formula IV, V and VI $R^1$ is methyl, 2-methoxyiminoethyl, bicyclo[1.1.1]pentan-1-yl, 2-fluoro-phenyl, 4-fluoro-phenyl, or 2,4-difluorophenyl; and $R^2$ is hydrogen.

* * * * *